(12) United States Patent
Branch et al.

(10) Patent No.: US 9,849,126 B2
(45) Date of Patent: Dec. 26, 2017

(54) STERILE OTIC FORMULATIONS

(71) Applicant: ENTRX LLC, Corsicana, TX (US)

(72) Inventors: Matthew Branch, Corsicana, TX (US); Vance Oglesbee, Corsicana, TX (US)

(73) Assignee: Entrx LLC, Corsicana, TX (US)

( * ) Notice: Subject to any disclaimer, the term of this patent is extended or adjusted under 35 U.S.C. 154(b) by 0 days.

(21) Appl. No.: 14/696,410

(22) Filed: Apr. 25, 2015

(65) Prior Publication Data

US 2015/0297588 A1  Oct. 22, 2015

Related U.S. Application Data

(63) Continuation-in-part of application No. 13/733,727, filed on Jan. 3, 2013, now Pat. No. 8,945,061.

(60) Provisional application No. 61/984,168, filed on Apr. 25, 2014.

(51) Int. Cl.
| | |
|---|---|
| A61K 31/496 | (2006.01) |
| A61K 47/06 | (2006.01) |
| A61K 31/573 | (2006.01) |
| A61K 9/00 | (2006.01) |
| A61K 31/4174 | (2006.01) |
| A61K 31/27 | (2006.01) |
| A61K 31/7048 | (2006.01) |
| A61K 47/44 | (2017.01) |
| A61K 31/47 | (2006.01) |
| A61M 5/00 | (2006.01) |

(52) U.S. Cl.
CPC .......... *A61K 31/496* (2013.01); *A61K 9/0046* (2013.01); *A61K 31/27* (2013.01); *A61K 31/4174* (2013.01); *A61K 31/47* (2013.01); *A61K 31/573* (2013.01); *A61K 31/7048* (2013.01); *A61K 47/06* (2013.01); *A61K 47/44* (2013.01); *A61M 5/00* (2013.01)

(58) Field of Classification Search
CPC ................................ A61K 47/06; A61K 31/47
See application file for complete search history.

(56) References Cited

U.S. PATENT DOCUMENTS

| | | | |
|---|---|---|---|
| 7,220,431 | B2 | 5/2007 | Sawchuk et al. |
| 8,030,297 | B2 | 10/2011 | Lichter et al. |
| 2005/0287219 | A1 | 12/2005 | Murthy |
| 2006/0194769 | A1* | 8/2006 | Johnson ............. A61K 31/353 514/114 |
| 2007/0078116 | A1* | 4/2007 | Lane .................... A61K 31/00 514/171 |
| 2009/0011045 | A1 | 1/2009 | Mertin et al. |
| 2010/0036000 | A1* | 2/2010 | Lichter ............... A61K 9/0024 514/772.1 |
| 2011/0263551 | A1 | 10/2011 | Slater |

FOREIGN PATENT DOCUMENTS

| | | |
|---|---|---|
| WO | WO0189496 | 11/2001 |
| WO | WO2009147144 | 12/2009 |

OTHER PUBLICATIONS

PCCA, Topical Bases Comparison Chart, Rev. Feb. 8, 2012.*
Narayan S, Swift A. Otitis extema: a clinical review. Br J Hosp Med (Lond). Oct. 2011;72(10):554-8.
Osguthorpe JD, Nielsen DR. Otitis externa: Review and clinical update. Am Fain Physician. Nov. 1, 2006;74(9):1510-6.
Rosenfeld RM, Singer M, Wasserman JM, Stinnett SS. Systematic review of topical antimicrobial therapy for acute otitis extema. Otolaryngol Head Neck Surg. Apr. 2006;134(4 Suppl):S24-48, abstract only.
Stergiopoulou T, Meletiadis J, Sein T, Papaioannidou P, Tsiouris I, Roilides E, et al. Comparative pharmacodynamic interaction analysis between ciprofloxacin, moxifloxacin and levofloxacin and antifungal agents against Candida albicans and Aspergillus fumigatus. J Antimicrob Chemother. Feb. 2009;63(2):343-8.
Stergiopoulou T, Meletiadis J, Sein T, Papaioannidou P, Tsiouris I, Roilides E, et al. Isobolographic analysis of pharmacodynamic interactions between antifungal agents and ciprofloxacin against Candida albicans and Aspergillus fumigatus. Antimicrob Agents Chemother. Jun. 2008;52(6):2196-204.
Hahn YH, Ahearn DG, Wilson LA. Comparative efficacy of amphotericin B, clotrimazole and itraconazole against *Aspergillus* spp. An in vitro study. Mycopathologia. Sep. 1993;123(3):135-40, abstract only.
Johnson MD, MacDougall C, Ostrosky-Zeichner L, Perfect JR, Rex JH. Combination antifungal therapy. Antimicrob Agents Chemother. Mar. 2004;48(3):693-715.
Robert Sander, Otitis Extema: A practical Guide to Treatment and Prevention, Am. Fam. Physician., Mar. 1, 2001; 63 (5):927-937, abstract only.
Genete G., et al., Development and Validation of HPTLC Assay Method for Simultaneous Quantification of Hydrocortisone and Clotrimazole in Cream and Applying for Stability Indicating Test, J. Chilean Chem. Soc. 57(3) 1199-1203 (2012).
Sugar, et al., Effectiveness of Quinolone Antibiotics in Modulating the Effects of Antifungal Drugs, Antimicrobial Agents and Chemotherapy, vol. 41, No. 11, Nov. 1997, p. 2518-2051.
Kumar, et al., Treatment of Otitis Extema in Dogs Associated with Malassezia Pachydermatis, Indian Vet. J., Jul. 2002; 79:727-729.
Search report of EP13735820.6.
Munguia & Daniel,Ototopical antifungals and otomycosis: A review,International Journal of Pediatric Otorhinolaryngology (2008) 72, 453-459.

* cited by examiner

*Primary Examiner* — Johann R Richter
*Assistant Examiner* — Genevieve S Alley
(74) *Attorney, Agent, or Firm* — Boulware & Valoir

(57) ABSTRACT

The present disclosure describes a sterile formulation and method for treating an ear infection, especially otomycosis and otitis externa, by administering a one-time only treatment comprising an antibiotic, and antifungal, and an optional anti-inflammatory in a thick, otic carrier. In one embodiment, the sterilization comprises e-beam irradiating ingredients the formulation while heat-sterilizing other ingredients before combining under sterile condition.

14 Claims, 3 Drawing Sheets

STERILE OTIC FORMULATIONS

PRIOR RELATED APPLICATIONS

This application claims priority to U.S. Provisional Application Nos. 61/984,168, filed on Apr. 25, 2014; 61/585,031, filed Jan. 10, 2012; 61/625,407, filed Apr. 17, 2012; and, 61/649,663, filed May 21, 2012; and to U.S. Non-provisional application Ser. No. 13/733,727, filed Jul. 11, 2013. Each is incorporated by reference herein in its entirety for all purposes.

FIELD OF THE DISCLOSURE

The disclosure relates to an antifungal/antibacterial/anti-inflammatory formulation for treating ear infection, especially chronic otitis, and methods for making the formulation sterile and stable.

BACKGROUND OF THE DISCLOSURE

Ear infections, especially fungal ear infections, are common ear disorders, often occurring in warm and humid climates. Fungal otitis externa is a fungal infection of the external auditory canal and associated complications. It has been reported that as high as 30.4% of otitis externa patients exhibit symptoms of fungal otitis or inflammatory conditions of the ear.

Common symptoms of ear fungal infection include otalgia, otorrhea, hearing loss, aural fullness, pruritus and tinnitus. Several factors that may cause or enhance the rate of fungal infection include humid climate, the presence of cerumen (ear wax) acting as a support for fungal growth, configuration of the ear canal, weak immune function, diabetes, increased use of ototopical antibiotics, prolonged use of broad-spectrum antibiotics, use of systemic steroids, pregnancy, hearing aids with occlusive molds, trauma, and bacterial infections.

Common fungi that cause otitis externa are *Aspergillus niger* and *Candida albicans*, and treatment thereof can be tailored against these fungi. Other fungi may also cause otitis externa, and can also be treated by respective therapeutic agents. It is debatable whether identification of the causal agent is necessary for determining the appropriate treatment. One school of thought believes that the treatment should be based on the susceptibility of the identified species, whereas others believe that the treatment should based on efficacy and characteristics of the drug regardless of the causing microbes. An experienced Ear, Nose and Throat physician (ENT) can now routinely treat fungus without cultures, mostly by identifying the characteristic fungal elements on exam, and apply topical acidifying agents or specific antifungals. Thus, practitioners can identify the organism, or just treat the likely organisms empirically according to best practices, as desired.

Currently, there are four main classes of drugs for the treatment of fungal infections, including polyenes, azoles, nucleoside analogs and enchinocandins. The mechanism of action of the polyene and azole families involves an essential chemical component called ergosterol found in the fungal cell membrane. The drug binds to ergosterol and creates a polar pore in the fungal membranes, which results in the leaking of ions and other molecules from within the cell, which in turn kills the cell. The nucleoside analogs interfere with nucleotide synthesis, which prevents proper energy production, metabolism and signaling of the cell. Echinocandins are a novel class of antifungal agents, acting by interfering with cell wall biosynthesis. However, echinocandins are known to be embryotoxic, and dose adjustment is required for patients having liver diseases.

To date, most reported treatment involves a solution, cream, powder or ointment to be topically applied multiple times for a period of time from one week to one month. See, e.g. Table 2 of Munguia et al., "Ototopical antifungals and otomycosis: A review", *Int'l J. of Pediatric Otorhinolaryngology* (2008) 72, 453-459. The prolonged treatment regimen causes inconvenience to the patients because either they have to visit a primary care physician or otolaryngologist multiple times, or for self-administered drugs, patients often forget to apply the drugs according to instruction, resulting in secondary proliferation of fungus and bacteria that may further extend the treatment period.

In addition, many drugs do not have complete efficacy for infection caused by multiple agents, and this can again prolong treatment times. Moreover, pure liquid form of drugs, such as ear drops, are less effective for treating chronic otitis externa especially because the liquids egress from the ear canal very rapidly; and, not all infected areas within the ear canal can be reached by the liquid because of gravity, especially in the upper half of the ear canal. Creams and ointments, in contrast, often remain in the ear and then have to be removed by the ENT.

U.S. Pat. No. 7,220,431 discloses a method for administering a pharmacological agent to the middle ear of a mammal by applying a formulation to the tympanic membrane of the mammal. The method does not teach how to treat an infection occurring at the auditory canal, such as otitis externa. The formulation is characterized by having a viscosity of less than 100,000 cps, and the formulation forms a gel after application to the tympanic membrane. However, the practical application of this patent may be problematic because once the ear canal is occluded, additional ear drops cannot be introduced. In addition, the solidified gel can be hard to remove by the patients after the infection symptoms are resolved. If the solidified gel remains too long within the ear canal after releasing all the active ingredients, recurrence of fungal and bacterial infection is likely.

U.S. Pat. No. 8,030,297 discloses a method for treating otic disorders selected from Meniere's disease, autoimmune ear disease, otitis media, acoustic trauma induced sensorineural hearing loss, drug-induced sensorineural hearing loss, sensorineural hearing loss, idiopathic sensorineural hearing loss, vertigo, and tinnitus. The method requires intratympanic administration of a pharmaceutical composition comprising a thermoreversible aqueous gel having 16% to 21% by weight of polyoxypropylene and polyoxyethylene and from 1 mg/ml to 70 mg/ml of a multiparticulate anti-inflammatory corticosteroid. The "intratympanic" administration and the targeted disorders make it clear that this patent does not treat otitis externa. Also, the patent does not teach the use of any antifungal agent for treating fungal infection.

There are also a couple of veterinary products available for animal use. POSATEX OTIC SUSPENSION™ by Intervet®/Schering-Plough Animal Health® contains Orbifloxacin, Mometasone Furoate Monohydrate and Posaconazole in a suspension. However, it has limited efficacy (against *Pseudomonas aeruginosa* and the yeast *Malassezia pachydermatis*) and the orbofloxacin is only approved for use in dogs. Further, it is required to be used daily for 7 consecutive days.

TRI-OTIC™ by Med-Pharmex® contains Gentamicin Sulfate, Betamethasone Valerate, and Clotrimazole. However, this formula also requires twice daily application into the ear canal for 7 consecutive days. Further, gentamicin is ototoxic and has limited efficacy (against *Malassezia pachydermatis*, formerly *Pityrosporumcanis*, and/or bacteria susceptible to gentamicin).

There are also a few combinations approved for use in humans, but all are of very limited efficacy. CIPRODEX® by Alcon® is 0.3% ciprofloxacin and 0.1% dexamethasone in a suspension. However, it has no efficacy against fungus, and is directed for twice daily use for seven days. CIPRO HC® a similar formulation containing ciprofloxacin and hydrocortisone and has the same limitations. Also CIPRO HC® is not sterilized and cannot meet the FDA mandate for sterilized otic medications. CORTISPORIN, available generically, contains neomycin and polymyxin B sulfates and hydrocortisone otic solution, but has the same limitations, and requires 3-4 applications a day for up to 10 days. Neomycin is also known for its ototoxicity.

Therefore, there is still a need for a medical formulation and method for treating fungal ear infections, such as otomycosis and otitis externa, that requires only a single administration and yet is still capable of eradicating a spectrum of fungal and bacterial infections and the coincident inflammation. There is a particular need for a formulation that is capable of maintaining the active agents within the ear canal of a patient such that only a single dose of the formulation is required to achieve a high cure rate of otomycosis and otitis externa.

Additionally, it has been documented that tympanic membrane perforations can be observed in fungal otitis externa. See Song et al., "Fungal otitis externa as a cause of tympanic membrane perforation: a case series." *Ear Nose Throat J.*, 2014 August; 93(8):332-6. FDA mandates all otic medications to be sterilized for this reason, and therefore there is the need for a long-lasting, single-dose and sterilized treatment high efficacy.

Furthermore, some of the above discussed Active Pharmaceutical Ingredients (API) have not been proven stable to heat or irradiate, and thus there are no commercial products with these API's that are sterile. Therefore, it would be beneficial if a formulation could be developed that was stable to sterilization methods.

SUMMARY

The present disclosure relates to formulations, methods and devices for treating chronic otitis externa that requires a one-time only administration, while retaining very high efficacy against a broad spectrum of fungus and bacteria. The formulation comprises a therapeutically effective amount of at least two of three agents: one or more antibacterial agents, one or more antifungal agents, and one or more anti-inflammatory agents, together with a thickened base that is flowable, but thick enough to egress from the ear in more than two days and less than 7 days. The formulations are described in US20130178801, expressly incorporated by reference herein in its entirety for all purposes. These various formulations are sterilized, providing a sterile pharmaceutical that does not introduce viruses or other microbial fauna to the already infected and inflamed ear.

Preferred embodiments include one, two or preferably all three of an azole antifungal agent, a thiocarbamate antifungal agent, and a polyene antifungal agent. This can be combined with an antibacterial, such as fluoroquinolone antibiotics, and, optionally, a corticosteroid anti-inflammatory agent. Together, these make up the active ingredients that eradicate a broad spectrum of fungal infections and any accompanying bacterial infection and inflammation. The formulation may also benefit from combination with anesthetics or analgesics. For example, benzocaine, which is already approved for otic use, can provide significant pain relief.

With the single-dose formulation of the presently disclosed formulation, complications due to patients' non-compliance in following dosing instructions can be eliminated. Additionally, the optimal approach of applying the Active Pharmaceutical Ingredients ("APIs") directly to the infected area results in less bacterial community resistance due to a considerably lower one-time dose, thereby keeping bacterial resistance to a minimum.

The use of a viscous carrier in the formulation makes it possible for the formulation to remain in viscous form once it is administered inside the ear canal and heated up by body temperature. Because of the high viscosity, the entire therapeutic formulation remains in contact with the infected ear canal for a prolonged time and the active ingredients can be continuously released for two to four days. Yet, the formulation eventually egresses, and no follow up visit is required for removal.

The viscous carrier can be any otologically acceptable material with the desired viscosity and that achieves the goal of maintaining the formulation within the ear canal for a prolonged period of time, preferably at least 5 days, yet is flowable enough at room temperature to be administered. Choosing different carriers may change the physical nature of the formulation, but not the therapeutic effect. For example, a person skilled in the art may so choose the carrier to make the formulation in fluid, foam, cream, ointment, or other otologically acceptable form.

Thickeners can be completely natural, like waxes, and also synthetic or semi-synthetic polymers and the like, including polysaccharides, proteins, alcohols, silicones or waxes. Suitable thickeners may include bees wax, candelilla wax, carnauba wax, paraffin, Ozokerite wax, cetyl alcohol, corn starch, glyceryl stearate, guar gum, gum Arabic, xanthan gum, lanolins, microcrystalline wax, acrylate polymers, polyalphaolefins, HE-Cellulose, PEG-150 Distearate, sorbitol, stearic acid, stearylpalmitate, Poloxamer 407, and the like.

The preferred thickeners are water insoluble or have low water solubility for longevity, and are not ototoxic. Preferred carriers include a combination of mineral oil and thickener, such as the proprietary blend of low density polyethylene known as PCCA Plasticized™ (PCCA US, TX, Cat. No. 30-3211). Even more preferred is a blend of 10-25%, 15-21% or 18% of United States Pharmacopoeia (USP) or National Formulary (NF) paraffin brought to 100% (ww) with USP or NF mineral oil.

The carrier is characterized in that it remains a thick fluid in the preferred embodiment for human patients and capable of staying inside the ear canals after being applied to a subject's ear canal and heated to the body temperature of about 37° C. Inventors' own experiments (data not shown) indicate that the formulation is a non-Newtonian fluid that has a varying viscosity when shear force is applied thereto. For a non-Newtonian fluid, the viscosity is more difficult to measure with certainty, and it is therefore not defined in this disclosure.

Although thick, the formulation remains a flowable fluid that can be applied by an application or administration unit, such as a syringe and a needle. The viscous fluid stays within the ear canal and remains in contact with the infected portion of the tissue. This allows the active ingredients within the formulation to be continuously released for a prolonged period of time, preferably at least 3 days, more preferred at least 4 days, and ideally 5 days, or even 6-7 days, thus continuously treating the fungal and bacterial infections, as well as the inflammation accompanied with the infections. More to the point, since the thick fluid will be in place for a prolonged period of time, the continuously released active ingredients will also maintain the hygiene within the ear canal by preventing the proliferation of fungi and bacteria. Additionally, the viscous nature of the formulation allows it to gradually egress from the ear canal (or be absorbed) after symptoms are resolved.

Generally speaking, antibacterial or antifungal APIs such as clotrimazole, etc. are not sterilized for topical use because the skin is not sterile.

Clotrimazole, for example, is stable in the solid state under normal storage conditions, but degrades upon exposure to humidity and light, and presumably other forms of irradiation as well. Further, stability typically decreases on solubilization, and in fact it is already known that in hydrocortisone and clotrimazole combinations, both drug substances were degraded on heating under reflux in 1M HCl at 80° C. and also upon treatment with 3% and 30% hydrogen peroxide. Unlike hydrocortisone, clotrimazole was found to be resistant to degradation on heating under reflux in thermal stress.

Ciprofloxacin and clotrimazole, however, showed relatively good heat resistance. Dexamethasone, on the other hand, showed poor heat resistance and ionizing radiation is therefore a better option for sterilization. We then experimented with other sterilization options.

We have now tested the herein described drugs, both in combination and as sole active ingredient (each in a wax and mineral oil vehicle) in a variety of non-terminal sterilization methods and have discovered a few combinations of methods that are satisfactory for sterilizing these diverse ingredients.

Based on these results, it is now possible to formulate a single use otic drug combination and sterilize the formulation with heat treatment for certain ingredients before combining the sterilized ingredients under sterile condition for packaging. Because 11% of fungal otitis externa results in perforation of the tympanic membrane, any compound applied to the external canal could end up in the middle ear. The current mandate of the FDA is that all otic suspensions with access to the middle ear be sterile. Therefore, a product with the current characteristics as disclosed herein can be manufactured sterile and would be beneficial due to the high likelihood of inadvertent entry into the middle ear. Thus, a sterilized product will not introduce any microbial, viral or other pathogen to an ear that is already traumatized by infection. Furthermore, a sterile product will have increased shelf life due to the lack of organisms that may feed off ingredients.

As used herein, "heat treatment" or "heat sterilization" refers to sterilizing the pharmaceutical composition with heat and maintaining the pharmaceutical formulation at a temperature for a period of time to eliminate or kill all forms of life, including transmissible agents, such as bacteria, fungi, viruses, spore forms, etc. The temperature is high enough and the duration is long enough to achieve sterilization while not degrading the active ingredients in the pharmaceutical composition.

As used herein, "ionizing radiation" refers to radiation with enough energy so that, during an interaction with an atom, the radiation can remove tightly bound electrons from the orbit of an atom, causing the atom to become charged or ionized. The sterilizing effect of ionizing radiation is used for sterilizing the pharmaceutical formulation. Examples of ionizing radiation suitable for this disclosure include but not limited to: e-beam irradiation and gamma irradiation.

As used herein, "ear infection" means fungal and/or bacterial infection in the ear. The location of the infection is primarily the auditory canal. In a preferred embodiment, the term ear infection includes otomycosis, and chronic and acute otitis externa.

As used herein, "active ingredient" means the substance of a pharmaceutical drug that has therapeutic effect against the disorder to be treated, either directly or when converted in the body to the active form.

As used herein, "fluoroquinolone" means the class of fluoroquinolone antibiotics generally bearing the following chemical structure:

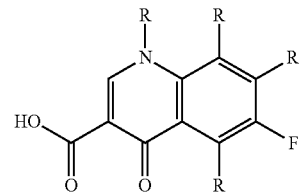

wherein R can be the same or different functional groups. Examples of fluoroquinolone that can be used in the presently disclosed formulations include, but are not limited to, ciprofloxacin, ofloxacin, levofloxacin, gatifloxacin, moxifloxacin, gemifloxacin, norfloxacin, danofloxacin, difloxacin, enrofloxacin, ibafloxacin, marbofloxacin, orbifloxacin, sarafloxacin, and combinations thereof.

As used here, "azole antifungal" includes triazoles and imidazoles. Triazole means either one of a pair of isomeric chemical compounds with molecular formula $C_2H_3N_3$, which has a five-membered ring of two carbon atoms and three nitrogen atoms. The pair of isomers have the following general structure:

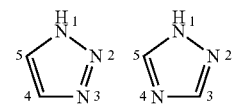

Triazoles are synthetic agents that can reduce the concentration of ergosterol, which is essential in normal cytoplasmic membrane of fungus. Examples of triazole antifungals that can be used in the presently disclosed formulations include, but not limited to, albaconazole, efiaconazole, isavuconazole, itraconazole, fluconazole, posaconazole, ravuconazole, terconazole, voriconazole and combinations thereof.

Imidazole is an organic compound with the formula $(CH)_2N(NH)CH$ in a 1,3-$C_3N_2$ ring having the following general structure:

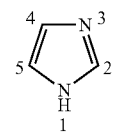

Imidazoles are also synthesized agents that can reduce the concentration of ergosterol that is essential in normal cytoplasmic membrane of fungus. Examples of imidazoles include bifonzaole, butoconazole, clotrimazole, econazole, fenticonazole, isoconazole, ketoconazole, luliconazole, miconazole, omoconazole, oxiconazole, sertaconazole, sulconazole and tioconazole.

As used herein, "thiocarbamate antifungal" means a family of organosulfur compounds that have the following general formula:

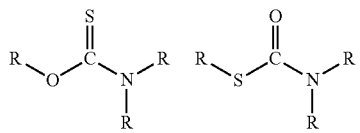

Examples of thiocarbamate antifungals that can be used in the presently disclosed formulations include, but are not limited to, tolnaftate and tolciclate, and combinations thereof. Tolnaftate acts by distorting hyphae and inhibiting the mycelial growth of susceptible fungi that cause skin infections, and has been recommended in refractory cases of otomycosis. It has been shown to be non-ototoxic.

As used herein, "corticosteroid" means a class of steroids having anti-inflammatory effect that may include, but are not limited to, amcinonide, betamethasone benzoate, betamethasone dipropionate, betamethasone valerate, clobetasol propionate, clocortolonepivalate, desonide, desoximetasone, dexamethasone, dexamethasone sodium phosphate, diflorasonediacetate, fluocinonide, fluocinoloneacetonide, flurandrenolide, fluticasone propionate, halcinonide, halobetasol propionate, hydrocortisone, hydrocortisone butyrate, hydrocortisone valerate, mometasonefuroate, prednisolone acetate, triamcinolone acetonide, and combinations thereof.

As used herein, "polyene antifungal" means a macrocyclic polyene with a heavily hydroxylated region on the ring opposite the conjugated system, and examples of polyene antifungal that can be used in the presently disclosed formulations include, but are not limited to, nystatin, amphotericin B and the combination thereof.

As used herein, "thickener" means otically acceptable additives that increase viscosity of the formulation. The thickener may make the overall formulation as auris-acceptable viscous fluid when the temperature rises to body temperature. Examples of thickeners that can be used in the presently disclosed formulations include, but not limited to, low-density polyethylene, poloxamers, waxes and the combination thereof. Mineral oil can be added to adjust the viscosity of the thickener.

As used herein, "administration unit" or "application unit" means a unit that is capable of storing a therapeutic agent and administering or delivering the therapeutic agent to a target area of a subject. Typical administration units include, but are not limited to, a syringe coupled with a needle or a tube, e.g., via a standard luer lock or luer connector. The needle or tube can be customized as described in US20130178801.

As used herein, "flowable" means a fluid having a viscosity less than 100,000 cPs at room temperature. Formulations that are a bit too thick for easy use with a given administration unit can be warmed to body temperature for use, and this has the added benefit of reducing patient discomfort on application.

As used herein, "partial" or "partially" heat sterilized and/or e-beam irradiation sterilized refers to a part of the composition or the active ingredients underwent heat sterilization and a part of the composition or the active ingredients underwent e-beam irradiation.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the disclosure, such as instructions for use, special packaging, preservatives, antioxidants and the like. The active pharmaceutical ingredients are considered material.

When a drug is referred to be name herein, all active salts, isomers, and derivatives thereof are considered to be included.

All percentages are by weight, unless indicated otherwise.

The following abbreviations are used herein:

| ABBREVIATION | TERM |
| --- | --- |
| API | Active Pharmaceutical Ingredients |
| ENT | Ear, Nose and Throat physician |
| RP-HPLC Chromatogram | Reverse phase High Performance Liquid Chromatography |
| CIP | Ciprofloxacin |
| Clot | Clotrimazole |
| Dex | dexamethasone |

DETAILED DESCRIPTION

Figure 1:
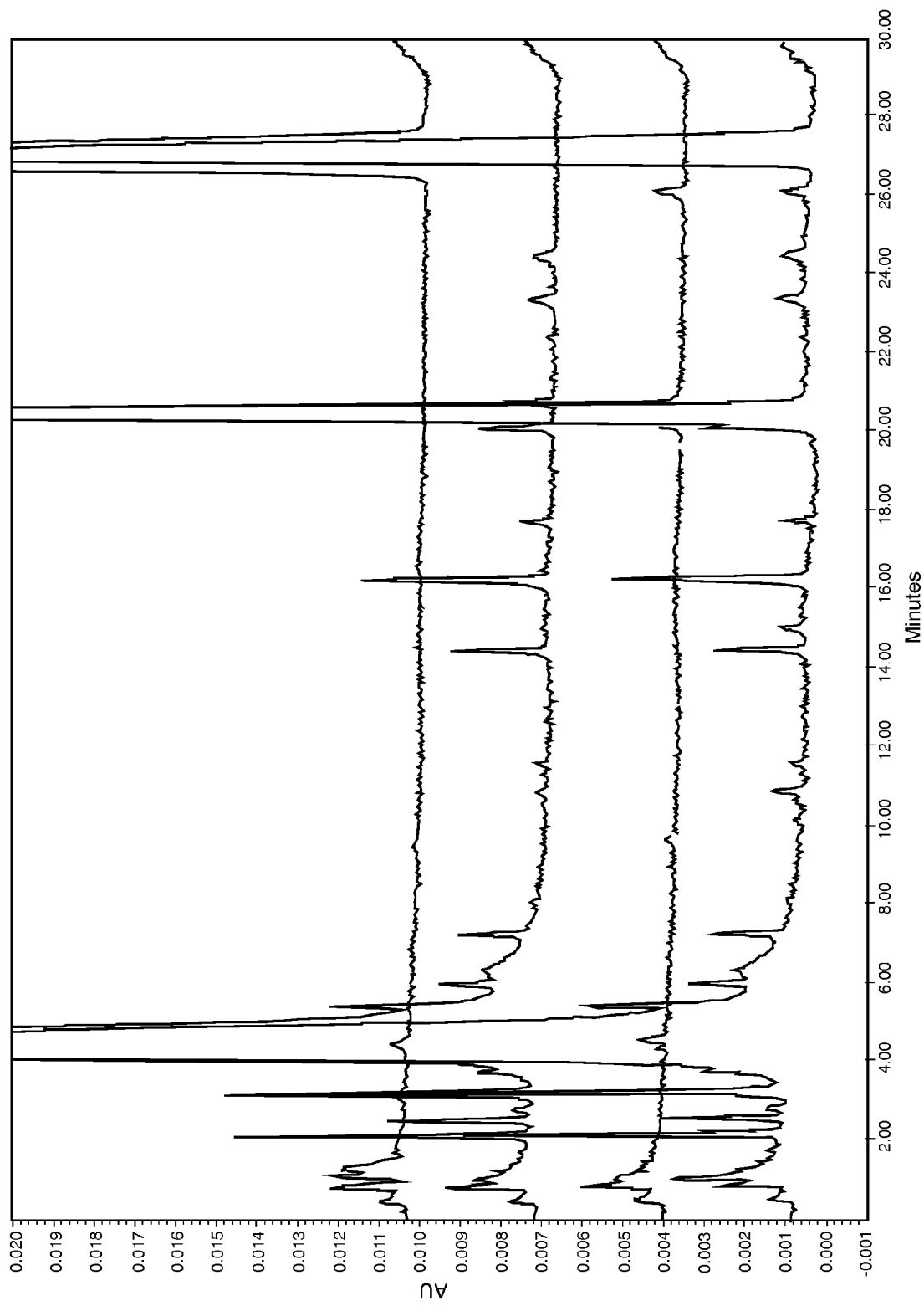
FIG. 1 shows RP-HPLC Chromatogram of RHM-11 and the individual components at 254 nm.

The present disclosure provides a novel sterile formulation and method for treating ear fungal infections, especially otitis externa. The sterile formulation and method of the present disclosure make it possible to treat and even eradicate the chronic otitis externa by one-time only administration of the formulation to the ear canal.

The disclosure provides a novel sterile formulation for treating fungal ear infection, comprising an antifungal, an antibiotic and an optional anti-inflammatory agent in a thick carrier at ear or body temperature.

In one embodiment, azole active ingredients, such as synthetic imidazoles like clotrimazole, and fluoroquinolone such as ciprofloxacin, in carrier including mineral oil and paraffin wax are first heat sterilized at about 110-130° C. for about 1-3 hours in a sterile vessel while being stirred, mixed and homogenized. After the heat treatment is completed, the vessel is cooled to about 50-80° C., while the stirring, mixing and homogenizing continues.

Dry, micronized and sterile dexamethasone powder, which may be pre-sterilized by e-beam irradiation, is then added to the vessel. The completely mixed and homogenized contents of the vessel are then cooled and added to syringes under sterile conditions. The syringes are then capped and sealed in sterile and opaque foil packages for labeling and transport.

Electron beam processing or e-beam irradiation is a process that uses electrons, usually of high energy, to treat an object for a variety of purposes. This may take place under elevated temperatures and nitrogen atmosphere. Possible uses for electron irradiation include sterilization and to cross-link polymers. Electron energies typically vary from the keV to MeV range, depending on the depth of penetration required. The irradiation dose is usually measured in Gray (Gy) but also in megarads (Mrads), where 1 Gy is equivalent to 100 rad.

The heat sterilization temperature and duration can vary, as long as proper sterilization results can be obtained. In one embodiment, the temperature is 110 to 130° C., and the duration is 1 to 3 hours. In another embodiment, the temperature is about 121° C. and the duration is about 1.5 hours.

The cooling temperature prior to adding the dexamethasone is preferably not too high to cause degradation to dexamethasone, while still high enough to maintain sterility. In one embodiment, the cooling temperature is 50 to 70° C. In another embodiment, the cooling temperature is about 60° C.

In a preferred embodiment, the disclosure provides a novel sterile formulation for treating fungal ear infection, comprising 0.01% to 1% by weight of a fluoroquinolone, 0.1% to 2% by weight of an azole antifungal, 0.1% to 2% by weight of a thiocarbamate, optionally 0.01% to 2.5% by weight of a corticosteroid, and 50,000 to 200,000 unit/ml of a polyene antifungal; 10% to 70% of thickener, and 30% to 90% of mineral oil. Other therapeutically appropriated bases can also be also be utilized in the present disclosure in place of the thickener without affecting the efficacy of the formulation.

A particularly preferred formulation is triturated and micronized dexamethasone that can be e-beam sterilized at about 5 kGy, but can be higher, e.g., <15 kGy. 3 mg/ml ciprofloxacin, 10 mg/ml clotrimazole in a mixture of wax and mineral oil are first heat-sterilized by heating the mixture to about 121° C. for 1.5 hours. After the ciprofloxacin and clotrimazole mixture is cooled to about 60° C., dexamethasone (which may or may not be e-beam sterilized) is added. In an alternative embodiment, 10 mg/ml clotrimazole in a mixture of wax and mineral oil is first heat-sterilized by heating the mixture to about 121° C. for about 1.5 hours. 3 mg/ml Ciprofloxacin in a mixture of wax and mineral oil is sterilized by ionizing radiation; triturated and micronized dexamethasone is also sterilized separately by ionizing radiation. After cooling the clotrimazole mixture to about 60° C., sterilized ciprofloxacin and dexamethasone are then added.

In a preferred embodiment, the fluoroquinolone is selected from the group consisting of: ciprofloxacin, ofloxacin, levofloxacin, gatifloxacin, moxifloxacin and the combination thereof, and more preferably the fluoroquinolone is ciprofloxacin or ofloxacin.

In a preferred embodiment, the azole antifungal is selected from the group consisting of: clotrimazole, ketoconazole, itraconazole, fluconazole, miconazole, econazole, butoconazole, oxiconazole, sulconazole, terconazole, and the combination thereof, and more preferably the azole antifungal is clotrimazole, ketoconazole, itraconazole, miconazole or the combination thereof. New generation azole antifungals including posaconazole and voriconazole can also be used.

In a preferred embodiment, the thiocarbamate antifungal is tolnaftate.

In a preferred embodiment, the corticosteroid is selected from the group consisting of: amcinonide, betamethasone benzoate, betamethasone dipropionate, betamethasone valerate, clobetasol propionate, clocortolonepivalate, desonide, desoximetasone, dexamethasone, dexamethasone sodium phosphate, diflorasonediacetate, fluocinonide, fluocinoloneacetonide, flurandrenolide, fluticasone propionate, halcinonide, halobetasol propionate, hydrocortisone, hydrocortisone butyrate, hydrocortisone valerate, mometasonefuroate, prednisolone acetate, triamcinolone acetonide, and the combination thereof. More preferably, the corticosteroid is dexamethasone, hydrocortisone, triamcinolone acetonide or the combination thereof.

In a preferred embodiment, the polyene antifungal is nystatin.

In a preferred embodiment, the carrier comprises mineral oil and a thickener. In a particularly preferred embodiment, it comprises 11-21% or 18% paraffin in mineral oil.

In a preferred embodiment, the method for treating ear infection comprises the following step: applying, one time only, a sterile formulation into the ear canal of a mammal, said formulation as described herein, together with thickener and mineral oil; wherein the formulation is viscous enough to stay inside the ear canal for 2 to 7 days after applying to the ear canal of the mammal, and wherein the formulation releases the active ingredients continuously for at least 3 days. In some embodiments, before applying the formulation to the ear canal, the method further comprises the step of debriding infectious and inflammatory debris from the ear canal.

In another embodiment, the disclosed is a sterile formulation for treating ear infection, comprising: one or more antifungal agents; one or more antibacterial agents; one or more anti-inflammatory agents; and a carrier, wherein said carrier retains said active ingredients in an ear for 2-7 days and then egresses or is absorbed.

In a preferred embodiment, the sterile formulation comprises ciprofloxacin, dexamethasone and clotrimazole in an aurally acceptable carrier. Preferably, 0.1-10% ciprofloxacin, 0.1-10% dexamethasone and 0.1-10% clotrimazole are used, most preferred is 0.3% ciprofloxacin, 1% clotrimazole, and 0.1% dexamethasone in a suitable carrier as described herein.

In a preferred embodiment, the mammal that can be treated with the formulation and method of the present disclosure includes humans, canines, felines, bovines, ovines, porcines, equines, as well as other mammals commonly treated by veterinarians for ear infections.

Other embodiments that are included in the scope of the disclosure include any one or more of the following, in any combination:
A formulation for treating ear infection, comprising active ingredients for treating fungal and bacterial infections, comprising: a fluoroquinolone antibacterial; an azole antifungal; and an optional corticosteroid;
a otically acceptable carrier that includes at least one thickener so that the formulation is capable of delivery to the ear canal of a mammal in a flowable fluid form but upon introduction into the ear canal the formulation remains in the ear canal for at least 3 days releasing said active ingredients. Preferably, this formulation is partially sterilized with heat and optionally partially sterilized by ionizing radiation before combined together.

A formulation for treating ear infection, wherein the fluoroquinolone antibacterial and the azole antifungal are heat-sterilized at a temperature of at least 120° C. for 1.5 hours and cooled to 60-80° C., then combined with an e-beam sterilized corticosteroid under sterile condition.

A formulation for treating ear infection, comprising active ingredients for treating fungal and bacterial infection comprising: about 0.3% by weight of ciprofloxacin; about 1% by weight of a clotrimazole; optionally about 0.1% by weight of a dexamethasone; in a thick carrier about 10-25% of wax; and about 75-90% of mineral oil.

A formulation wherein said carrier comprises about 10-90% of said thickener.

A formulation wherein said carrier comprises 75-90% mineral oil and 10% to 25% of wax.

A formulation wherein said carrier comprises 82% of said mineral oil and 18% of paraffin.

A formulation wherein said formulation comprises 0.01% to 2% by weight of said fluoroquinolone that is selected from the group consisting of: ciprofloxacin, ofloxacin, levofloxacin, norfloxacin, gatifloxacin, gemifoxacin, moxifloxacin and combinations thereof.

A formulation wherein said fluoroquinolone is ciprofloxacin, ofloxacin or the combination thereof.

A formulation wherein said formulation comprises 0.1% to 2.5% by weight of said azole antifungal that is selected from the group consisting of: clotrimazole, ketoconazole, itraconazole, fluconazole, miconazole, econazole, butoconazole, oxiconazole, sulconazole, terconazole, and the combination thereof.

A sterile formulation wherein said azole antifungal is clotrimazole, ketoconazole, itraconazole, miconazole and the combination thereof.

A formulation wherein said formulation comprises 0.01% to 2.5% by weight of said corticosteroid that is selected from the group consisting of: amcinonide, betamethasone benzoate, betamethasone dipropionate, betamethasone valerate, clobetasol propionate, clocortolonepivalate, desonide, desoximetasone, dexamethasone, dexamethasone monosodium phosphate, diflorasonediacetate, fluocinonide, fluocinoloneacetonide, flurandrenolide, fluticasone propionate, halcinonide, halobetasol propionate, hydrocortisone, hydrocortisone butyrate, hydrocortisone valerate, mometasonefuroate, prednisolone acetate, triamcinolone acetonide, and the combination thereof.

A formulation wherein said corticosteroid is dexamethasone, hydrocortisone, triamcinolone acetonide or the combination thereof.

A formulation wherein said formulation comprises 50,000 to 200,000 unit/ml of a polyene antifungal, wherein said polyene antifungal is nystatin.

A formulation as herein described wherein said dexamethasone is sterilized with e-beam irradiation at about 5 kGy.

A method wherein said formulation include clotrimazole or other azole drug.

A method wherein said formulation include clotrimazole or other azole drug and ciprofloxacin or other fluoroquinolone drug.

A method wherein said formulation include clotrimazole, ciprofloxacin and optionally dexamethasone, wherein said ciprofloxacin and clotrimazole are sterilized with heat treatment at a temperature of at least 120° C. for 1.5 hours.

A method of treating otis externa, comprising administering a single dose of the formulation herein described to a patient's ear.

Heat Treatment

Heat treatment of Ciprofloxacin (Cip), Clotrimazole (Clot) and Dexamethasone (Dex) in the paraffin/mineral oil matrix has been tested. The composition was heat treated at 121° C. for more than 1.5 hours. The results indicate that Ciprofloxacin (Cip) and clotrimazole (Clot) did not show significant degradation. Dexamethasone or dexamethasone mono sodium phosphate, on the other hand, degraded under those heat treatment conditions to a significant extent (data not shown).

Heat and Ethanol Treatments

To investigate the feasibility of manufacturing a sterile drug product using heat sterilization at 121° C., the drug product matrix with Ciprofloxacin and Clotrimazole was heated, and after reducing the temperature to 50-80° C., an ethanol solution of Dexamethasone was added to the drug matrix, wherein the ethanol solution can be sterile filtered before addition to prevent degradation of this heat sensitive Dexamethasone. Ethanol can be subsequently removed by applying low pressure to the reaction vessel.

Formulations (ENTRx 401) were manufactured in the laboratory. The batch sizes of the ENTRx 401 formulations ranged from 2 mL to 250 mL (Table 1). ENTRx 401 formulations containing all three drug substances Ciprofloxacin (Cip) (3 mg/mL), Clotrimazole (Clot) (10 mg/mL) and Dexamethasone (Dex) (1 mg/mL) were prepared by adding the Cip and Clot to the liquid mineral oil and wax solution at 60° C. followed by heating to 121° C. and stirring for up to 5 hours.

An ethanol solution of Dex was prepared at 11-12.5 mg/mL and slowly added to the matrix at 50-80° C. under reduced pressure, which resulted in the removal of the ethanol by evaporation. The chemical stability of each individual API component in the ENTRx 401 prototype formulations was evaluated at different time points during the heat sterilization process by RP-HPLC analysis using RP-HPLC methods adapted from the US Pharmacopeia.

Quinazole Rx 7049360 is a composition that contains Ciprofloxacin (3 mg/mL), Clotrimazole (Clot) (10 mg/mL) and dexamethasone monosodium phosphate (DexP) (1 mg/mL) and is used as a standard for comparison to the experimental formulations.

Figure 2:
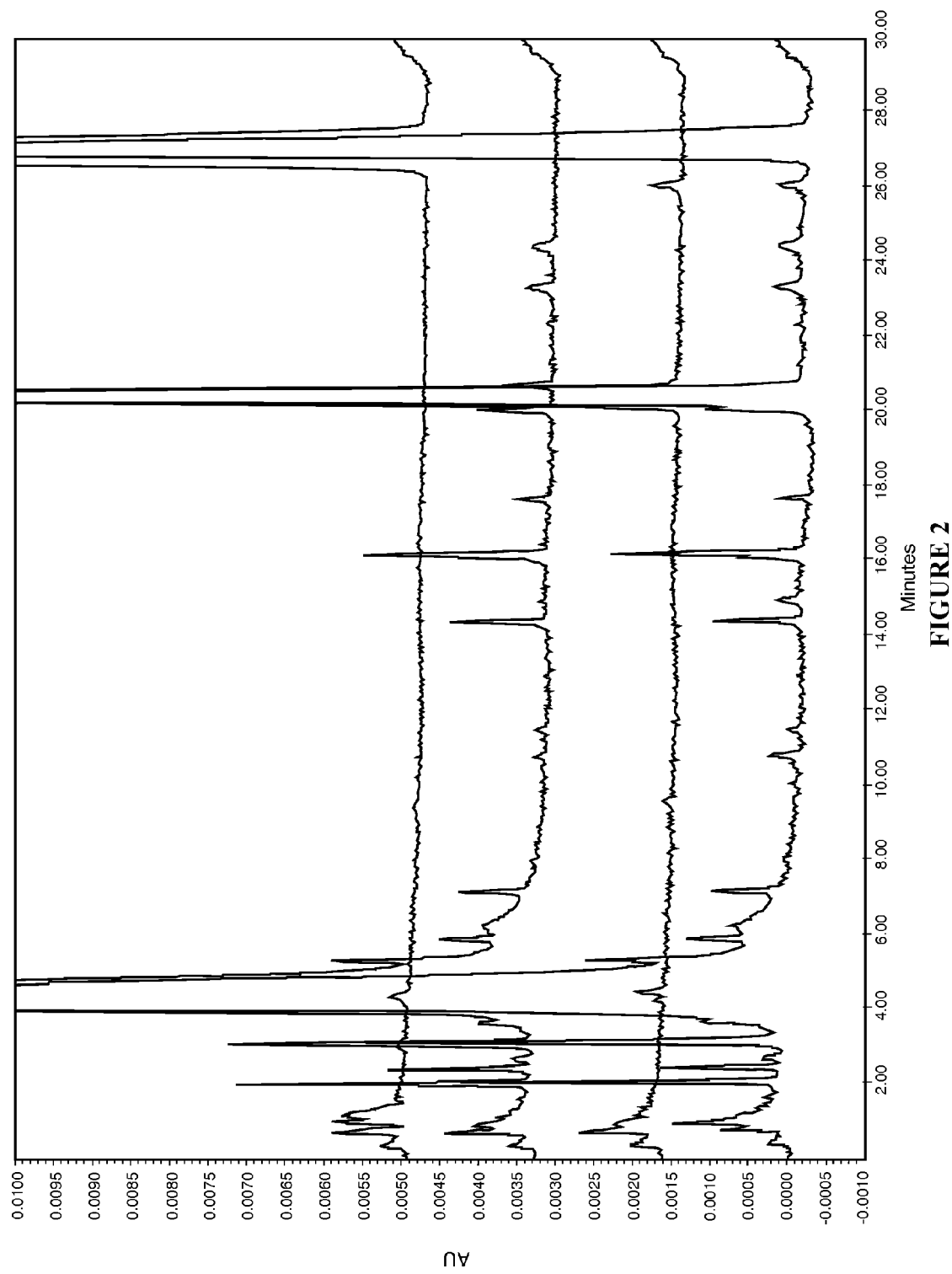
FIG. 2 shows RP-HPLC Chromatogram of RHM-11 and the individual components at 278 nm.

In one experiment (RHM-11) (FIGS. 1 and 2), 4.5 g of wax and 20.5 mL of mineral oil were placed in a round bottom flask, heated to 60-70° C. while stirring and adding 75 mg of Cip and 250 mg of Clo and keeping it for 1.5 hours at 120-125° C. After cooling to 86° C., a solution of a solution of 26 mg of dexamethasone in 2.2 ml of ethanol was slowly added while stirring vigorously. The temperature was raised to 100° C. for 10 minutes and vacuum was applied to remove the ethanol prior to cooling the material. The end point of removal of the ethanol was determined visually by observing the condensing ethanol on the condenser. Cooling was initiated 5 minutes after ethanol condensation was no longer observed.

In another experiment (RHM-12) a Büchi rotary evaporator equipped with a HPLC tubing through the stop cock reaching from the outside of the rotary evaporator to the inside of a flask was used to allow addition of ethanol solution while under vacuum. 45 g of paraffin wax and 205 mL of mineral oil were placed in a beaker and heated to 60° C., 750 mg of Cip and 2500 mg of Clot were added and the mixture was heated to 120° C. for 1.5 hours. The material was then transferred into a 500 mL round bottom flask, the water bath of the Büchi evaporator was set to 62° C. and the round bottom flask was allowed to equilibrate for 15 min while spinning to allow the material to cool down.

A vacuum was applied and 250 mg of Dex dissolved in 20 mL of ethanol was slowly added over a period of 30 min. During the addition under vacuum the ethanol immediately evaporated when it came in contact with the spinning flask as evidenced by foaming of the material. The beaker containing the solution was then rinsed with 5 mL of ethanol and the rinse solution was slowly added to the flask as well. After the addition, a full vacuum (10-12 Torr) was applied for 20 minutes to drive the additional ethanol out of the DP matrix. The material was then cooled down while being stirred.

The instrumental set up for these experiments uses a beaker with a stir bar on a stirrer with heating capacity and a thermometer. The heat sterilization process was developed following a succession of small scale experiments in a beaker under different temperature and time conditions and at different scales ranging from 2 mL to 250 mL to find the desired conditions to execute the ultimate experiment in the Büchi Evaporator (Table 1). The experimental conditions and progression of the experiments including observations, results and conclusions are described in Table 1.

TABLE 1

Progression of Heat Sterilization Experiments Leading to Buchi Evaporator Experiment

| Experiment Code (Scale) | API's | Method/Conditions | Observation/Results/Notes |
|---|---|---|---|
| JFT-1 (2 mL) | Cip; Clot; Dex | Added suspension of all three drugs to matrix at 100° C.; kept DP at 100 to 120° C. for up to 5 hours | Ethanol does not form a homogenous solution with liquid wax and mineral oil. Ethanol can be removed by evaporation at high temperature above boiling point. Solubility of Clot in ethanol sufficient; solubility of Dec (phosphate) and Cip insufficient. Water as solvent for drug is not recommended; drug precipitates in water droplets during evaporation |
| JFT-2 (10 mL) | Cip; Clot; Dex | Added all three drugs as sieved powders to matrix at 90° C.; kept DP at 122 to 125° C. for up to 4 hours followed by cooling to room temperature | Stirring is important to keep drug products in suspension. Some drug will dissolve at higher temperature and some will not and remain suspended. Cooling even during stirring is very inhomogenous; hardens first at glass wall and progresses to center of beaker. Stirring at all times during temperature changes is important to keep DP homogenous. First finding that Clot and Cip survives high temperature treatment (heat sterilization) but Dex does not |
| RHM-2 (5 mL) | Cip; Clot; DexP | Sample 1-matrix only; Sample 2-matrix + Cip; Sample 3-matrix + Clot; Sample 4-matrix + Dex; Sample 5-matrix + Cip, Clot, Dex | Samples were made at 60° C. and then heated to 121° C. Samples were pulled at 1, 2 and 3 hours. Cip and Clot were stable under those conditions. Dex did degrade to a significant extent |
| RHM4-1 (50 mL) | Cip; Clot; DexP | Cip added as solid at 60° C. Clot added as solid at 60° C. DexP added as solid at 60° C. | Minimal impurities, impurity profile looks equivalent to quinazole 60° C. for 30 min |
| RHM4-2 (50 mL) | Cip; Clot; DexP | Cip added as solid at 121° C. Clot added as solid at 121° C. DexP added as solid at 121° C. | Sample is identical to RHM-4-1 121° C. for 10 min |
| RHM4-4 (50 mL) | Cip; Clot; Dex P | Cip added as solid at 121° C. Clot added as solid at 121° C. DexP added as solid at 121° C. under $N_2$ | There is no protecting effect of N2 atmosphere 121° C. for 1.5 Hours DexP added under $N_2$ blanket |
| RHM8-2 (33 mL-100 mL split in three parts) | Cip; Clot; Dex P | Cip added as solid at 121° C. Clot added as solid at 121° C. DexP added as solution in water at 60° C. | 121° C. for 1.5 Hours 60° C. for 1 hr No significant difference between this formulation and Quinazole Lower peak area of DexP (inhomogenous distribution) |
| RHM8-3 (33 mL-100 mL split in three parts) | Cip; Clot; Dex P | Cip added as solid at 121° C. Clot added as solid at 121° C. DexP added as solution in water at 60° C., vacuum | 121° C. for 1.5 Hours 60° C. for 1 hr No significant difference between this formulation and Quinazole Water does not evaporate with the vacuum in a significant manner Lower peak area of DexP (inhomogenous distribution) |
| RHM-10 (50 mL) | Cip; Clot; DexP | Cip added as solid at 121° C. Clot added as solid at 121° C. DexP added as solid at 60° C. | Dexamethasone instead of Dexamethasone monosodium phosphate used 121° C. for 1.5 hours Temperature dropped to 60° C. No significant degradation of any of the API's |

TABLE 1-continued

Progression of Heat Sterilization Experiments Leading to Buchi Evaporator Experiment

| Experiment Code (Scale) | API's | Method/Conditions | Observation/Results/Notes |
|---|---|---|---|
| RHM-11 (25 mL) | Cip; Clot; DexP | Cip added as solid at 121° C. Clot added as solid at 121° C. DexP added as solution in ethanol at 60° C. | Dexamethasone instead of Dexamethasone monosodium phosphate used 121° C. for 1.5 hours Temperature dropped to 60° C. Vacuum was applied Temperature was brought up to 80° C. for 10 min to evaporate ethanol No significant degradation of any of the API's |
| RHM-12 (250 mL) | Cip; Clot; DexP | Cip added as solid at 121° C. Clot added as solid at 121° C. DexP added as solution in ethanol at 60° C. | Dexamethasone instead of Dexamethasone monosodium phosphate used A Büchi rotary evaporator was used Process conditions: 121° C. for 1.5 hours Vacuum was applied and the ethanol solution was added under vacuum. Significant evaporation of the ethanol under those conditions was achieved Full vacuum was applied for 20 min to drive off ethanol No significant degradation of any of the API's |

Figure 3:
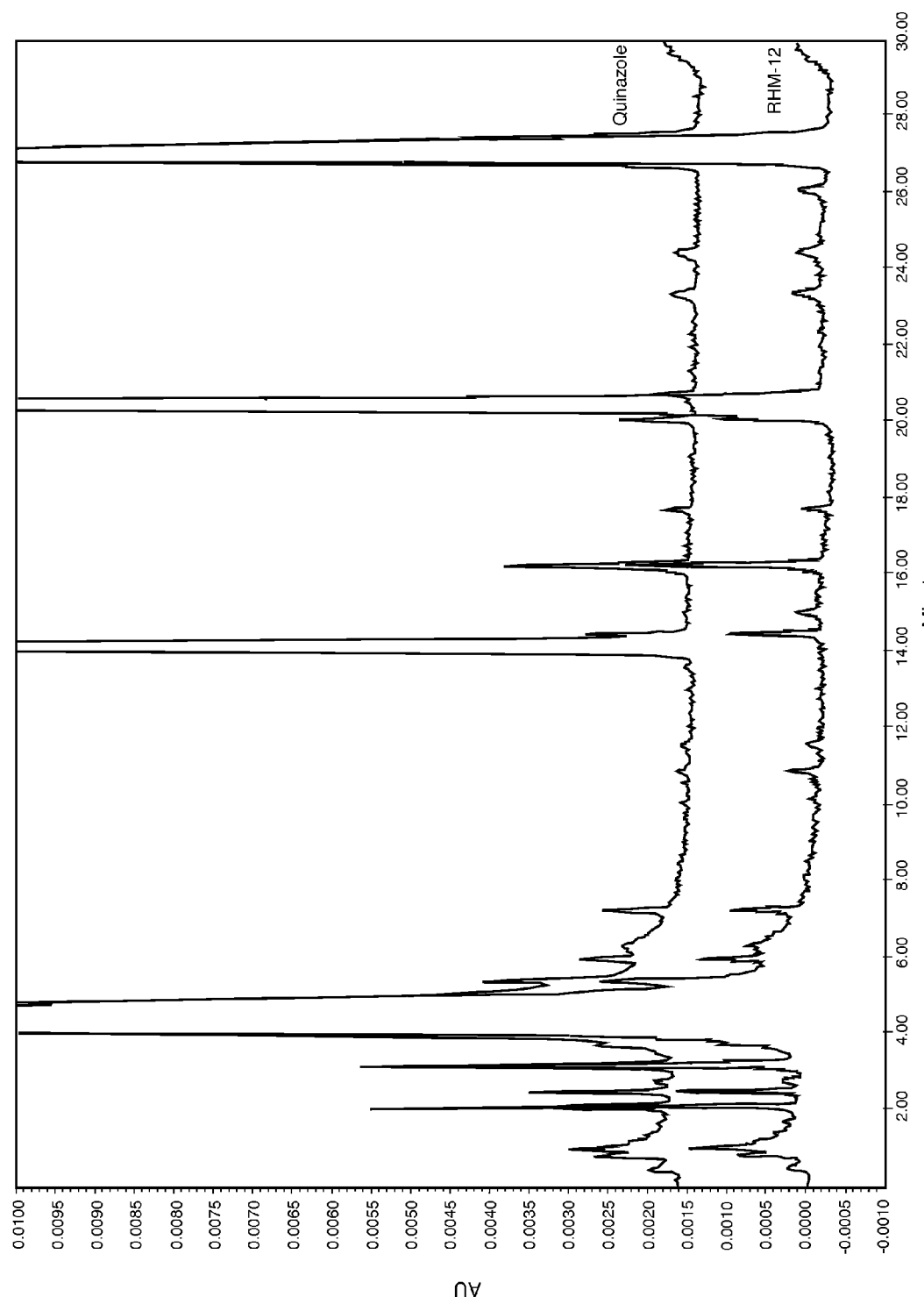
FIG. 3 shows comparative RP-HPLC Chromatogram of RHM-12 and Quinazole Rx 7049360.

The chemical stability of all three APIs, when formulated as described above, in the Büchi Evaporator was found to be acceptable (Table 2). The RP-HPLC chromatograms of RHM-12 were comparable to the Quinazole (Rx 7049360) shown in FIG. 1. It should be noted that this formulation of Quinazole used Dexamethasone monosodium phosphate (DexP) while Dexamethasone (Dex) was used for RHM-12. The impurity profile is almost identical with some very minor impurities at the retention times (RT) of 15 and 26 minutes, respectively (FIG. 3).

The physical stability of ENTRx 401 based on appearance and visual inspection was comparable to ENTRx 401 prepared and provided by ENTRx. However, a stratification or separation of phases was observed in the formulations that were left on the bench for several days at ambient temperatures. RHM-12 after storage at ambient temperature above 25° C. stratified into two phases. This was observed regardless of the experimental conditions and/or raw materials used. It was also observed with Quinazole (by ENTRx) compared side by side with RHM-12 on the lab bench at ambient temperatures.

It was noted that the temperature in the lab outside of working hours was significantly higher than during working hours. Two samples of Quninzole or RHM-12 were mixed thoroughly and one was placed in controlled room temperature storage (20±3° C.) and the other was placed on the bench. Within two days, the bench top samples stratified again while the material stored at controlled room temperature (20±3° C.) remained homogeneous. When these samples was taken out of the controlled storage and placed on the bench stratification occurred within two days. These results indicate that there is a temperature sensitivity of the DP matrix leading to phase separation of the matrix independent whether the DP matrix was initially subjected to high heat (121° C.) or not. Analysis of top and bottom layer indicates that the API content is not homogeneous. In some instances, the APIs appear to have been settling at the bottom of the container as well.

The purity of the APIs in RMH-12 and Quinazole was estimated based on the purity and impurity profiles of the individual APIs formulated separately in the DP matrix assuming that if degradation occurs that the degradation rate will be independent in the presence of one or more API in the DP matrix with no protective or destabilizing synergistic effects. Comparative RP-HPLC analyses of RHM-12 and Quinazole produced by different processes showed no major differences in the content and impurity profiles of the APIs except Dex was used in RHM-12 and DexP in Quinazole (FIG. 3). Exposure of the individual APIs in the DP matrix for up to 6 months at 2-8° C., 20° C. and 40° C. did not result in any measurable degradation and any differences among the three temperature conditions (Table 3).

Potential ethanol residuals in the DP matrix of RHM-12 and a control DP matrix not previously exposed to ethanol were tested by a validated GC-MS method. The results confirm that ethanol can be efficiently removed at 60° C. under vacuum in a Büchi Evaporator as the residual ethanol was found to be less than 40 ppm in RHM-12 which was found to be the detection limit of ethanol in the DP matrix (Table 2).

TABLE 2

Purity of Drug Product and Ethanol Content in Heat Sterilized ENTRx 401

| Experiment code (sale) | API's added | Estimation of Purity (254 nm) (%) | Estimation of Purity (278 nm) (%) | Approximate RP-HPLC RTs (min) | Heat Sterilization (hours) | Ethanol Content (PPM) |
|---|---|---|---|---|---|---|
| RHM-12 (250 mL) | Cip (powder) Clot (powder) Dex (solution) | Cip: 99.22% Clot: 99.92% Dex: 96.34% | Cip: 99.782% Clot: 99.76% Dex: 99.14% | Cip: 4.1 to 4.2 Clot: 26.1 to 16.2 Dex: 20.2 to 20.3 | Yes (1.5 hours) | <40 ppm |

TABLE 2-continued

Purity of Drug Product and Ethanol Content in Heat Sterilized ENTRx 401

| Experiment code (sale) | API's added | Estimation of Purity (254 nm) (%) | Estimation of Purity (278 nm) (%) | Approximate RP-HPLC RTs (min) | Heat Sterilization (hours) | Ethanol Content (PPM) |
|---|---|---|---|---|---|---|
| Quinazole (100 mL) | Cip (powder) Clot (powder) Dex (solution) | Cip: 99.61% Clot: 99.28% Dex: >99.5% | Cip: 99.94% Clot: 99.67% Dex: >98.65% | Cip: 4.1 to 4.2 Clot: 26.1 to 16.2 Dex: 13.7 to 13.8 | No | N/A |
| DP Matrix (control, 250 mL) | No APIs | N/A | N/A | N/A | Y | |

Note:
Main and impurity peaks in RHM-12 and Quinazole were assigned based on RTs and RTTs of peaks obtained with individual APIs standards, individual APIs in DP matrix and individual APIs in DP matrix exposed to 60° C. for 6 months (see Table 3). Purity of Clot is estimated as its only sole y impurities co-elutes with main peak of Cip.

TABLE 3

Purity of Individual APIs in DP Matrix at 6 Months and Three Different Temperatures

| API | Conditions | Purity 1(%) | Purity 2(%) | API | Conditions | Purity 1(%) | Purity 2(%) |
|---|---|---|---|---|---|---|---|
| CIP | Standard | 99.69 | 99.54 | DEXP | Standard | 100.00 | 99.75 |
| CIP | 4° C. | 99.68 | 99.52 | DEXP | 4° C. | 98.83 | 99.82 |
| CIP | 20° C. | 99.68 | 99.51 | DEXP | 20° C. | 98.74 | 99.66 |
| CIP | 40° C. | 99.73 | 99.55 | DEXP | 40° C. | 99.30 | 99.48 |
| CLOT | Standard | 98.58 | 100.00 | DEX | Standard | | 99.10 |
| CLOT | 4° C. | 99.49 | 100.00 | | | | |
| CLOT | 20° C. | 99.82 | 100.00 | | | | |
| CLOT | 40° C. | 99.71 | 100.00 | | | | |

To investigate whether the viscosity and the melting characteristics of the ENTRx 401 drug product changes as a result of the heat sterilization process, viscosity measurements of the DP matrix were conducted with a Brookfield spindle viscometer and an adapter to measure small sample quantities. Rather than looking at the absolute viscosity the purpose of the experiment was to examine if there is a viscosity difference between the materials. Although the composition was determined to be non-Newtonian fluid and the viscosity therefore could not be accurately measured, both materials, RHM-12 and Quinazole Rx#7049360 (as control) were measured at 34-35° C. and at 40° C. and in both cases almost identical results were obtained (data not shown). Therefore, it is believed that the heat sterilization does not affect the viscosity characteristics of the composition.

Medical Treatments

About 100 patients (work is ongoing and thus the exact number of patients is subject to change) diagnosed with otomycosis, chronic and acute otitis externa were selected for the treatment using the three formulations, ages from 26 months old to 78 years old. The formulations tested are repeated below:

| | | | |
|---|---|---|---|
| Ciprofloxacin | 0.30% (297 mg) | Ciprofloxacin | 0.30% |
| Nystatin | 100,000 units/ml (1707 mg) | Nystatin | 100,000 units/ml |
| Itraconazole | 1% (990 mg) | Clotrimazole | 1% (990 mg) |
| Dexamethasone | 0.10% (99 mg) | Dexamethasone | 0.10% |
| Tolnaftate | 1% (990 mg) | Tolnaftate | 1% |
| Mineral Oil | ~40% | Mineral Oil | ~40% |
| PCCA Plasticizer | ~60% | PCCA Plasticizer | ~60% |
| Ciprofloxacin | 0.30% | Ciprofloxacin | 0.30% |
| Clotrimazole | 1% | Clotrimazole | 1% |
| Dexamethasone | 0.10% | Dexamethasone | 0.10% |
| Mineral Oil | ~40% | Mineral Oil | 82% |
| PCCA Plasticizer | ~60% | Paraffin | 18% |

After debriding the infectious and/or inflammatory debris from the ear canal, an appropriate amount of a formulation from above was administered to the infected ear canal such that all available space in the outer ear was filled. The formulations were stored in a syringe before use, and can be stored at room temperature without deteriorating the therapeutic effect. The syringe is preferably attached to an 18 gauge metal or rigid plastic tip with the distal 1 cm being soft and very flexible to avoid inadvertent injury to the ear drum of outer ear structures. However, other suitable delivery devices can also be used without deviating from the spirit of the present invention.

First the ENT doctor carefully placed the flexible needle inside the patient's auditory canal. Upon pressing the plunger, the therapeutic formulation was dispensed into the auditory canal and remains therein. Because of the flexible nature and rounded tip of the needle, doctors can minimize possible scratching when applying the therapeutic formulation. The dispensed thick fluid will fill in the space within the auditory canal, thereby contacting the infected area therein while preventing secondary infection in the ear canal.

After administration of the formulation, each patient was examined to ensure that the formulation remained within the ear canal. Cotton balls were provided at the outer ear canal (conchal bowl) to catch egress, but no attempt was made to "plug" the ear canal. Follow-up examination was performed between 7 to 14 days after initial treatment. In several instances, residue of the formulation was observed at day 14, indicating the formulation did maintain within the ear canal for as long as 14 days. Patients reported that symptoms relief occurred usually within three days, while hearing returned to normal within 5 to 7 days after treatment.

Visual examination as well as questionnaire from patients confirmed that no sign of infection existed after day 14 for all patients but two, who also had 98% of symptoms resolved. In other words, the formulation achieved at least 98% cure rate with a single treatment. The formulation of the present invention can continuously release the active ingredient to the infected area, thereby treating as well as preventing proliferation of secondary fungal/bacterial infection that may be caused by the condition within the ear canal occupied by the formulation.

In summary, at least 100 patients have been tested with the above formulations. Only 2 out of 100 patients failed to completely resolve their symptoms and nearly all in 2-4 days. The two patients who failed, required systemic antibiotics and essentially had complicated otitis externa or cellulitis. Further, patients on follow-up are already forming normal cerumen in an incredibly short interval. This is a sign of return to normal epithelial function that is typically not seen for weeks after otitis externa, and may indicate the emollient effects of the mineral oil formulation. It is a notable clinical finding that the inventors have NEVER seen with ear drops of any kind.

Preparing the formulation of the present disclosure can be performed with various compounding methods, as long as the final product has the desired characteristics, such as remaining flowable at both room temperature and body temperature, while remaining in the ear canal for a prolonged period of time and providing a continuous release of active ingredients. In particular, the methods of US20130178801 can be used, followed by e-beam irradiation at room temperature to the indicated dosage, or a combination of heat and ethanol sterilization can be used as described herein.

The novel sterilization of the ingredients is therefore believed to prevent further infection caused by unsterilized medication, especially in the case where the medication is supposed to stay in the ear for at least three days. The sterilized drug composition provides potent, effective, long-lasting and single treatment for ear infection that prevents repeated infection due to unsterilized medication. Furthermore, the sterilized drug composition is compliant with FDA regulation regarding otic medications.

The following references are incorporated by reference in their entirety.
1. Narayan S, Swift A. Otitis externa: a clinical review. Br J Hosp Med (Loud). 2011 October; 72(10):554-8.
2. Osguthorpe J D, Nielsen D R. Otitis externa: Review and clinical update. Am Fam Physician. 2006 Nov. 1; 74(9): 1510-6.
3. Rosenfeld R M, Singer M, Wasserman J M, Stinnett S S. Systematic review of topical antimicrobial therapy for acute otitis externa. Otolaryngol Head Neck Surg. 2006 April; 134(4 Suppl):S24-48.
4. Stergiopoulou T, Meletiadis J, Sein T, Papaioannidou P, Tsiouris I, Roilides E, et al. Comparative pharmacodynamic interaction analysis between ciprofloxacin, moxifloxacin and levofloxacin and antifungal agents against *Candida albicans* and *Aspergillus fumigatus*. J Antimicrob Chemother. 2009 February; 63(2):343-8.
5. Stergiopoulou T, Meletiadis J, Sein T, Papaioannidou P, Tsiouris I, Roilides E, et al. Isobolographic analysis of pharmacodynamic interactions between antifungal agents and ciprofloxacin against *Candida albicans* and *Aspergillus fumigatus*. Antimicrob Agents Chemother. 2008 June; 52(6):2196-204.
6. Hahn Y H, Ahearn D G, Wilson L A. Comparative efficacy of amphotericin B, clotrimazole and itraconazole against *Aspergillus* spp. An in vitro study. Mycopathologia. 1993 September; 123(3):135-40.
7. Johnson M D, MacDougall C, Ostrosky-Zeichner L, Perfect J R, Rex J H. Combination antifungal therapy. Antimicrob Agents Chemother. 2004 March; 48(3):693-715.
8. Munguia et al., Ototopical antifungals and otomycosis: A review, International J. of Pediatric Otorhinolaryngology (2008) 72, 453-459.
9. Robert Sander, Otitis Externa: A practical Guide to Treatment and Disclosure, Am. Fam. Physician., 2001 Mar. 1; 63(5):927-937.
10. U.S. Pat. No. 7,220,431 & U.S. Pat. No. 8,030,297
11. US20130178801
12. Genete G., et al., Development And Validation Of HPTLC Assay Method For Simultaneous Quantification Of Hydrocortisone And Clotrimazole In Cream And Applying For Stability Indicating Test, J. Chilean Chem. Soc. 57(3) 1199-1203 (2012).

While preferred embodiments of the present disclosure have been shown and described herein, such embodiments are provided by way of example only. Various alternatives to the embodiments can be optionally employed without deviating from the spirit of the present disclosure. The scope of the disclosure is defined by the following claims.

The invention claimed is:

1. A single-dose formulation for treating ear infection, comprising:
   a) active ingredients for treating fungal and bacterial infections, comprising:
      i) ciprofloxacin;
      ii) an azole antifungal; and,
      iii) dexamethasone;
   b) an otically acceptable carrier that includes at least one thickener so that the single-dose formulation is capable of a one-time delivery to the ear canal of a mammal in a flowable fluid form but upon introduction into the ear canal the formulation remains in the ear canal for at least 3 days releasing said active ingredients.

2. The formulation of claim 1, wherein said azole antifungal is sterilized with heat treatment, and said fluoroquinolone antibacterial is sterilized with heat treatment or ionizing radiation.

3. The formulation of claim 2, wherein said azole antifungal and said fluoroquinolone are both sterilized with heat treatment, and said heat treatment comprises heating the azole antifungal and/or the fluoroquinolone to at least 120° C. for 1-3 hours.

4. The formulation of claim 3, wherein the optional corticosteroid is added to the heat-treated azole antifungal and fluoroquinolone after the temperature is cooled to about 50-70° C.

5. The formulation of claim 4, wherein said optional corticosteroid is sterilized with e-beam irradiation at <15 kGy before adding to the heat treated azole antifungal and fluoroquinolone.

6. The formulation of claim 1, wherein said carrier comprises about 10-90% of said thickener.

7. The formulation of claim 1, wherein said carrier comprises 75-90% mineral oil and 10% to 25% of wax.

8. The formulation of claim 1, wherein said carrier comprises 82% of said mineral oil and 18% of paraffin.

9. The formulation of claim 1, wherein said formulation comprises 0.1% to 2% by weight of said azole antifungal that is selected from the group consisting of: clotrimazole, ketoconazole, itraconazole, fluconazole, miconazole, econazole, butoconazole, oxiconazole, sulconazole, terconazole, and the combination thereof.

10. The formulation of claim 1, wherein said formulation further comprises 50,000 to 200,000 unit/ml of a polyene antifungal, wherein said polyene antifungal is nystatin.

11. The formulation of claim 1, wherein said carrier comprises about 40% mineral oil and about 60% PCCA Plasticizer base, wherein said PCCA Plasticizer comprises butylated hydroxytoluene, polyethylene and mineral oil.

12. A sterile single-dose formulation for treating ear infection, comprising:
   a) active ingredients for treating fungal and bacterial infection comprising:
      i) about 0.3% by weight of ciprofloxacin;
      ii) about 1% by weight of a clotrimazole;
      iii) about 0.1% by weight of a dexamethasone; and
   b) about 10-25% of wax; and
   c) about 75-90% of mineral oil;
   d) wherein said ciprofloxacin and clotrimazole are sterilized with heat treatment at a temperature of at least 120° C. for 1-3 hours.

13. A method of treating otitis externa, comprising administering a single dose of the formulation of claim 1 to a patient's ear.

14. A method of treating otitis externa, comprising administering a single dose of the formulation of claim 12 to a patient's ear.

* * * * *